United States Patent [19]
Vander Heyden

[11] Patent Number: 5,307,668
[45] Date of Patent: May 3, 1994

[54] GAS DENSITY METER AND METHOD

[75] Inventor: William H. Vander Heyden, Mequon, Wis.

[73] Assignee: Badger Meter, Inc., Milwaukee, Wis.

[21] Appl. No.: 956,143

[22] Filed: Oct. 5, 1992

[51] Int. Cl.$^5$ .............................................. G01N 9/32
[52] U.S. Cl. .................................. 73/30.02; 73/23.38; 73/861.01
[58] Field of Search ................. 73/23.2, 23.28, 23.29, 73/30.01, 30.02, 30.03, 30.04, 861.01, 861.02, 861.03, 861

[56] References Cited

U.S. PATENT DOCUMENTS

| | | | |
|---|---|---|---|
| 3,701,280 | 10/1972 | Stroman | 73/23.2 |
| 4,285,245 | 8/1981 | Kennedy | 73/861 |
| 4,379,402 | 4/1983 | Herman, III | 73/23.2 |
| 4,527,418 | 7/1985 | Arcara | 73/30.01 |
| 4,677,841 | 7/1987 | Kennedy | 73/30.02 |
| 5,201,581 | 4/1993 | Vander Heyden et al. | 73/863.03 |
| 5,226,728 | 7/1993 | Vander Hayden | 73/196 |

Primary Examiner—Hezron E. Williams
Assistant Examiner—Michael J. Brock
Attorney, Agent, or Firm—Quarles & Brady

[57] ABSTRACT

Disclosed is a method and apparatus for determining the ratio of the flowing condition density of a pipeline gas (i.e. the density at a flowing temperature and pressure) to the base condition density of the pipeline gas (i.e. the density at a base temperature and pressure). A sample of the pipeline gas is tapped from the pipeline to a first chamber of fixed volume where its temperature is maintained at the temperature of the gas flowing in the pipeline and the pressure of the sample is equivalent to the pressure of the gas in the pipeline. The sample of gas is flowed from the first chamber at a constant mass flow rate and the time rate of change of the pressure in the first chamber is determined. The ratio is derived from the time rate of change of the pressure in the first chamber, and the flowing temperature and pressure. By determining the base condition density separately, the flowing condition density may then be determined.

14 Claims, 4 Drawing Sheets

GAS DENSITY METER AND METHOD

BACKGROUND OF THE INVENTION

In one aspect, the present invention relates to a method and instrumentation that measures, in real time, the density of a gas flowing in a pipeline. In this aspect, the invention can also measure a base condition density of the same gas where the base condition density corresponds to a density (i.e. mass/volume) of the gas determined as if the gas were at some defined base temperature and pressure condition. In a broader aspect, the present invention determines a ratio $$\frac{p_f}{p_b}.$$

of the measured flowing condition density compared to the base condition density. This ratio can be referred to as a volume correction ratio and can be used to translate a measured pipeline gas volumetric flowrate to a corresponding base condition volumetric flow rate.

Heretofore, accurate measurement of gas flowrates has often been difficult because accurate determination of gas density is important when measuring gas flowrates and gas supercompressibility effects gas density in ways that are not detectable by volumetric flowmeters. For instance, with differential pressure flowmeters (e.g., an orifice plate meter), the density term appears directly in the volume flow equation $$(\text{i.e. } \sqrt{\rho \Delta P}).$$

Also, with other flowmeters (such as turbine flowmeters), as well as with differential pressure flowmeters, the translation of volumetric flowrate to base conditions (i.e. volume correction ratio) is directly related to the density of the flowing gas.

Yet, at elevated gas pressure, computing gas density from the ideal gas law is inadequate and can be substantially wrong because the ideal gas law does not properly account for supercompressibility. If gas properties are well known, the difficulty can be partially alleviated because gas supercompressibility can be directly computed and accommodated in the calculations. However, if the gas is a variable mixture of unlike molecules, gas properties necessary to compute supercompressibility are unknown and difficult to measure.

Gas densities, volume correction ratios, and volumetric flowrates at base conditions are normally calculated using flow computers from contemporaneous measurements of several gas parameters. Generally, for determining volumetric flowrates at base conditions, the pipeline gas volumetric flowrate at pipeline conditions is measured, the gas temperature and pressure at pipeline conditions are measured, and the composition of the gas is measured. Gas composition is normally measured by a chromatograph. From this measured data, gas supercompressibility at both pipeline and base conditions is calculated and from that the density of the gas at pipeline and base conditions is calculated. When operating pressure is elevated (and supercompressibility effects cannot be ignored) gas supercompressibility is usually estimated from either virial equations of state or from correlations such as NX-19. Using virial coefficients is severely limited because the virial coefficients are functions of temperature, pressure, and composition, are largely unknown, and have significant real time uncertainties. Also, using correlations such as NX-19 is often inaccurate because the correlations can be inaccurate for many compositions.

An alternate method for determining volumetric flowrates at base conditions involves the Gerg Equations. The Gerg Equations estimate supercompressibility and density from knowledge of the heating value, the density of the gas at base conditions and the percentage of carbon dioxide and nitrogen in the exhaust of burned gas. Such measurements can be made using PMI's GB 3000 product (Precision Measurements, Inc., Tulsa, Okla.). The Gerg Equations allow more rapid computation of supercompressibility than the above described composition methods and are, therefore, preferred in applications at normal natural gas pipeline pressures. However, as with composition methods, extensive use of a flow computer is required to solve the Gerg Equations.

Moreover, each of the measurements recited above in describing both the composition method or the Gerg Equations method introduce the potential for measurement error. The aggregation of such errors can substantially influence accuracy. Because of this, it is common practice to frequently calibrate and maintain each individual measurement device.

In co-pending patent applications, Ser. No. 07/793,753, filed on Nov. 18, 1991, and Ser. No. 07/787,188, filed on Nov. 4, 1991, inventions are disclosed that among other things can determine the volume correction ratio of a pipeline gas from energy type measurements. These inventions involve the measurement of energy flowrate and energy content of a sample of gas tapped from the pipeline. A base condition volumetric flowrate of the sample gas can then be determined by the ratio of the energy flowrate of the sample gas to the energy content of the sample gas. These inventions also measure the ratio of the mass flowrate of the pipeline gas in the pipeline compared to the mass flowrate of the sample gas tapped from the pipeline. The volume correction ratio (or the base condition volumetric flowrate of the pipeline gas) can be calculated easily from the mass flowrate ratio and the base condition volumetric flowrate of the sample gas.

While it is desirable to measure energy flowrate and energy content in many applications, in applications where energy flowrate or energy content are not required (but where base condition volumetric flowrates are desirable), the energy measurement equipment provides excessive expense. Further, the inventions in these two co-pending patent applications are directed to monitoring combustible pipeline gas and are thus inappropriate for monitoring flows of non-combustible gas.

SUMMARY OF THE INVENTION

The object of the present invention is to provided an improved method and apparatus for measuring a volume correction ratio and a flowing condition density of a pipeline gas.

Another object of the present invention is to make these measurements without making energy type measurements.

The present invention is a method of apparatus that can determine a volume correction ratio for a gas (i.e. a ratio of a flowing condition density compared to a base condition density $$\frac{p_f}{p_b}),$$

and in another aspect can also determine a flowing condition density of a gas. It can make these determinations accurately in real time, without making several highly variable measurements, without making any energy type measurements, and without making excessive numeric calculations or correlations in a flow computer.

The present invention measures the volume correction ratio by measuring the temperature and pressure of sample gas tapped from a pipeline as it undergoes controlled expansion. Before the expansion, the sample gas is trapped to assure that it has the same composition as the pipeline gas. The rate of expansion of the trapped sample gas can be controlled in several ways, but it is preferred that the expansion be controlled by establishing mass flow at sonic conditions through a sonic nozzle. It is important that the expansion of the sample gas occur while the trapped sample gas is at substantially the same temperature as the pipeline gas being monitored. In a preferred embodiment, this is achieved by immersing a portion of the meter within the pipeline.

In particular, sample gas is tapped from the pipeline and flows to a first chamber having a fixed volume. A first valve controls the flow of sample gas into the first chamber. When the first valve is opened, sample gas flows into the first chamber preferably until the pressure in the first chamber equals the pressure in the pipeline.

The first valve is then closed and stops further pipeline gas from flowing into the first chamber. In order to measure the volume correction ratio, the sample gas temperature must be maintained at substantially the same temperature as the pipeline gas temperature. Sample gas flows from the first chamber and then through a flow restrictor located downstream of the first chamber. The flow restrictor is preferably a sonic nozzle. The sample gas pressure at the inlet of the flow restrictor is established by a pressure regulator so that gas flows from the first chamber at a substantially constant flowrate. If a sonic nozzle is used, the established pressure is sufficient so that the mass flow through the sonic nozzle is critical (i.e., the sonic nozzle inlet pressure is sufficient so that the mass flowrate through the sonic nozzle is proportional to the density and sonic velocity of the gas and nozzle cross-sectional area).

Flowing sample gas from the first chamber when the first valve is closed causes the pressure in the first chamber to reduce over time. The rate of change of the pressure in the first chamber is measured as the pressure in the first chamber decays. The temperature of pipeline gas being monitored is also measured.

The volume correction ratio is determined from the rate of change of pressure in the first chamber, the absolute pressure of the pipeline gas, and the absolute temperature of the pipeline gas. The determination can be done without restoring to estimates and approximations for supercompressibility.

The present invention eliminates the need to estimate or consider the effects of supercompressibility when determining gas density because the pressure rate of change measurements in the first chamber are made and used in density calculations directly.

In another aspect of the invention, the volume correction ratio (i.e. the ratio $$\frac{p_f}{p_b}$$

of the flowing condition density $p_f$ to the base condition density $p_b$) is used to determine the flowing condition density $p_f$ from a measured base condition density $p_b$. The preferred method and apparatus for measuring the base condition density $p_b$ are disclosed generally in U.S. Pat. No. 4,677,841 to Kennedy, et. al. It is preferred that the sonic nozzle of the present invention for measuring the volume correction ratio also be used as a pore where the square of the mass flow rate through the pore is inversely proportional to the density of gas flowing through the pore when the present invention measures the base condition density $p_b$.

To determine the base condition density $p_b$, it is preferred that the first valve be maintained open to allow sample gas to flow into the first chamber and therefrom; through the pressure regulator; and then into a second chamber also having a fixed volume. Also preferably; the flow into the second chamber is controlled by a second valve. The flow of sample gas from the second chamber is restricted by the pore. The mass flowrate through the pore is measured and from that mass flowrate measurement and a similar measurement of a reference gas which is made periodically, the base condition density $p_b$ of the sample gas can be determined.

In another preferred embodiment of the invention, volumetric flow signals are received from a volumetric flowmeter in the pipeline and the volumetric and mass flowrate in the pipeline at base conditions or pipeline conditions can be determined.

The aspect of the invention that measures the base condition density $p_b$ (i.e., U.S. Pat. No. 4,677,841 in conjunction with a reference gas) has proven to be accurate. Also, using a reference gas avoids the need to force the sample gas temperature and pressure to base conditions at the pore, such as 14.71 psia and 60° F., in order to make a base condition density $p_b$ measurement. This is because the density of the gas flowing through the pore is measured at ambient conditions and then translated to the base condition density through a prior knowledge of the reference gas base condition.

The foregoing objects and advantages of the present invention will appear from the following description. In the description, references are made to the accompanying drawings which form a part hereof and in which a preferred embodiment of the present invention is shown by way of illustration. Such embodiment does not necessarily represent the full scope of the invention however.

DETAILED DESCRIPTION OF THE PREFERRED EMBODIMENTS

The present invention includes many aspects, including the aspect of measuring a volume correction ratio $$\left(\frac{\rho_f}{\rho_b}\right)$$

without measuring a base condition density $\rho_b$. The preferred aspect of the present invention, however, involves the measurement of $\rho_b$ and is, therefore, discussed first.

In this description of the preferred embodiments of the invention, the apparatus of the preferred embodiment and its operation is first described. Then an analysis of the invention in scientific and mathematical terms is presented. Finally, operation of the present invention with a volumetric flowmeter is described.

APPARATUS OF THE PREFERRED EMBODIMENTS

Figure 1:
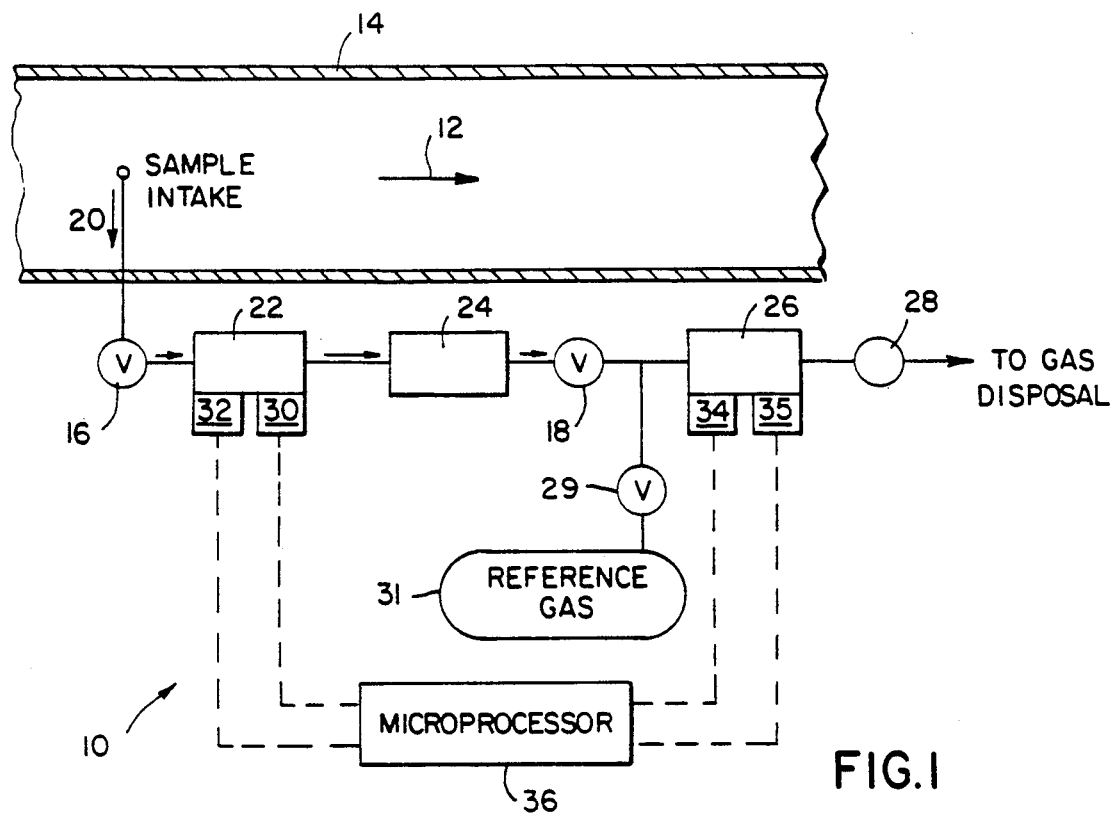
FIG. 1 is a schematic drawing of the fundamental apparatus of the preferred embodiment of the present invention.

In FIG. 1, a gas density meter of the present invention is designated generally as 10. The solid lines connecting elements of the gas meter 10 represent flow of sample gas and the dashed lines represent electrical signals.

The gas density meter 10 has two modes of operation: a base condition mode and a flowing condition mode. In the base condition mode, the meter 10 measures a base condition density $\rho_b$ of a pipeline gas 12 flowing through a pipeline 14 (i.e., the density of the gas at some designated base temperature, pressure, and composition). When the meter 10 is operating in the base condition mode, valve 16 is open and valve 18 cycles open and closed. In the flowing condition mode, the meter 10 measures a flowing condition density $\rho_f$ of the pipeline gas 12 flowing through the pipeline 14 (i.e., the density of the gas 12 at the temperature and pressure that it is flowing through the pipeline 14). When the meter 10 operates in flowing condition mode, valve 16 is closed and valve 18 is open. A complete measurement cycle constitutes operation in both the base condition and the flowing condition modes. Note that in applications where only a volume correction ratio $$\left(\frac{\rho_f}{\rho_b}\right)$$

is desired and it is not necessary to determine either the base or the flowing condition densities, it is not necessary to operate in the base condition mode.

Referring in particular to FIG. 1, the sample gas 20 is tapped from the pipeline 14 and flowed into a first fixed-volume chamber 22 when valve 16 is open. The volume of the first chamber 22 is small, about 5-10 cubic centimeters. The sample 20 gas fills the first chamber 22 until the pressure in the first chamber 22 is equal to the pipeline gas 12 pressure in the pipeline 14. The sample gas 20 then flows to a mechanical pressure regulator 24 where the pressure of the sample gas 20 is reduced, and if valve 18 is open, flows into a second fixed-volume chamber 26. The sample gas 20 then flows from the second chamber 26 through a pore 28.

When operating in the base condition mode, the flow of sample gas 20 through the pore 28 is controlled using valve 18. The pore 28 is operated in a special operating mode so that the square of the sample gas 20 mass flowrate through the pore 28 is inversely proportional to the density of the sample gas 20 at the time it is flowing through the pore 28. This special operating mode was discovered by Kennedy and is described in U.S. Pat. No. 4,677,841.

There are many ways to determine the sample gas 20 mass flowrate through the pore 28, but the preferred way is to measure a sample gas 20 pressure decay rate in the second chamber 26 and compare this to a reference gas 31 pressure decay rate, as now explained.

Opening valve 18 allows sample gas 20 into the second chamber 26. Closing valve 18 allows the pressure in the second chamber 26 to decay due to the flow through the pore 28. The pressure in the second chamber 26 is measured by pressure sensor 34. The rate of change of pressure in the second chamber 26 can be determined by comparing signals from the pressure sensor 34. The sample gas 20 pressure decay rate is then compared to a pressure decay rate of a standard or reference gas 31.

The reference gas 31 has a known composition and a known density $\rho_{ref}$ at base conditions (i.e. 60° F., 14.71 psia). About once a day, valve 18 is closed and valve 29 is opened for a referencing process. The referencing process usually requires a few cycles of operation (about 30 to 200 seconds). In the referencing process, the pressure decay rate of the reference gas 31 is measured in the same manner as the sample gas 20 pressure decay rate. Also, the temperature of the reference gas 31 in the second chamber 26 is measured by temperature sensor 35. The values of the reference gas 31 temperature and pressure decay rate are stored in the microprocessor 36.

The base condition density $\rho_b$ of the sample gas 20 can be determined relative to the known base condition density $\rho_{ref}$ for the reference gas 31 by multiplying by the ratio of sample gas 20 pressure decay rate compared to the reference gas 31 pressure decay rate. Also, changes in temperature from the time of the referencing process can be accounted for by measuring the temperature of the sample gas 20 in the second chamber 26, comparing the sample gas 20 temperature to the reference gas 31 temperature, and making a linear adjustment.

The above-described referencing process could be replaced by initial absolute calibration. However, frequent referencing eliminates longer term calibration drift.

After the base condition density $\rho_b$ has been determined during a measurement cycle, the valve 16 before the first chamber 22 is closed so that the flowing condition density $\rho_f$ can be determined. At the point in time when the valve 16 is closed, pressure in the first chamber 22 is initially at pipeline pressure. The pressure in the first chamber 22 is measured using a pressure sensor 30. The flow of sample gas 20 from the first chamber 22 is controlled by a non-venting mechanical pressure regulator 24 which reduces the sample gas pressure to a lower level, about 20-30 psig, after the sample gas 20 flows from the first chamber 22. Following the mechanical regulator 24, sample gas 20 flows into the second chamber 26 since the valve 18 should be open.

With the valve 18 open, the pressure applied to the pore 28 (i.e., the pressure in the second chamber 26) raises to the level of the regulator 24 output and is maintained at roughly that level by the regulator 24. The sample gas 20 flows through the pore 28 which now operates as a sonic nozzle 28 because of the higher applied pressure. The mechanical regulator 24 is set such that the pressure applied to the pore 28 (i.e. sonic nozzle 28) is sufficient to ensure critical or sonic flow during the flowing condition mode.

Volumetric flow through the sonic nozzle 28 is therefore constant throughout the flowing condition mode of each measurement cycle (i.e. the cycle of measured pressure decay in the first chamber 22). This is because the composition x of the sample gas 20 is fixed since closing valve 16 traps sample gas 20 in the first chamber 22. The composition x of the sample gas 20 that flows through the sonic nozzle 28 (i.e. pore 28) can and will vary from measurement cycle to cycle, but in any single measurement cycle, the composition x is fixed (because valve 16 closes), and the sonic nozzle 28 flowrate is therefore constant during that cycle.

As explained later under the Scientific and Mathematical Analysis, critical flow through a sonic nozzle 28 is the preferred manner of determining the mass flowrate of sample gas 20 at flowing conditions and at base conditions that exits the first chamber 22. Other types of flow restrictors, besides a sonic nozzle 28, such as orifices, capillaries, and venturis could be used, however. The term flow restrictor as used herein refers to a fluid device where the flow through the device corresponds to the applied gas pressure. It should also be noted that the analysis associated with Eqs. (11) through (15) is specifically for a sonic nozzle 28.

As molecules of sample gas 20 flow from the first chamber 22, the pressure in the first chamber 22 reduces and the pressure sensor 30 measures the changing pressure.

Figure 6:
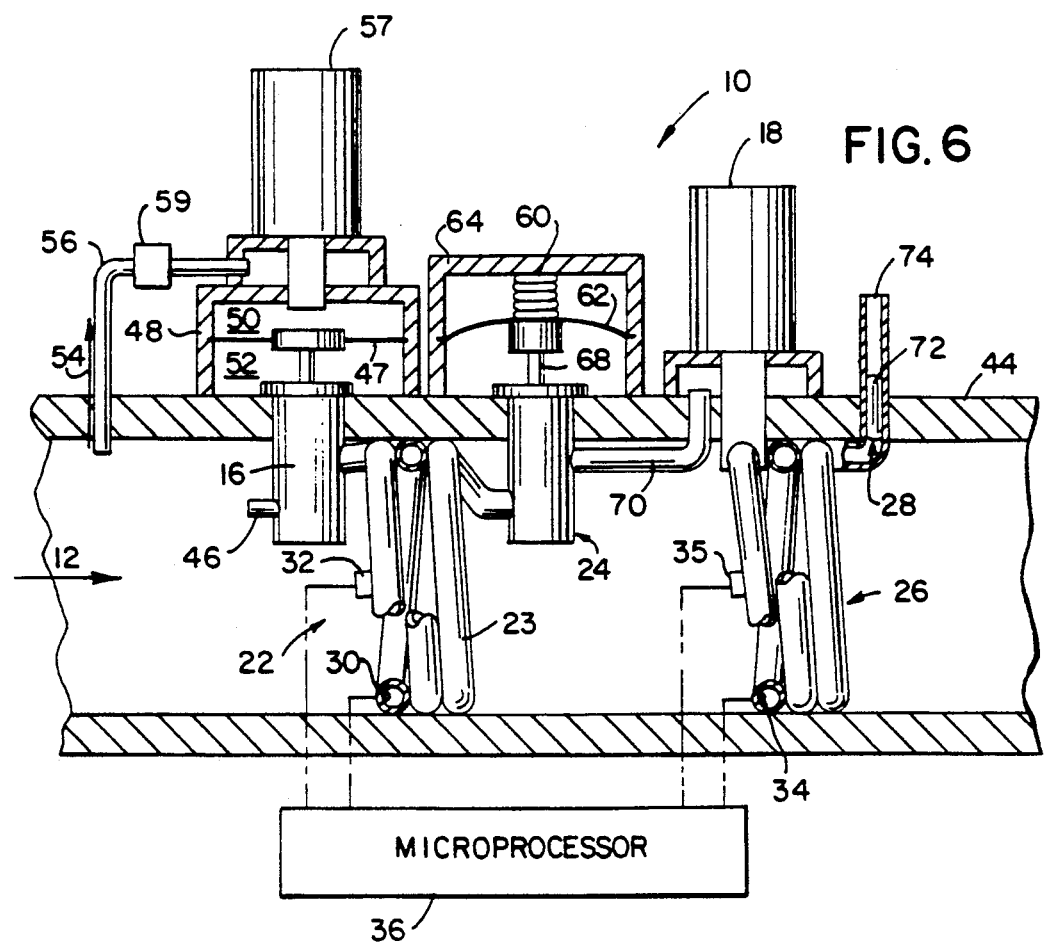
FIG. 6 is a schematic drawing showing the preferred method of installing the present invention.

The sample gas 20 must remain at pipeline gas temperature $T_f$ when the invention operates in flowing condition mode. Referring to FIG. 6, this may be done by inserting the unit into the pipeline 14.

In particular, the meter 10 shown in FIG. 6 is built into a meter body 44. The entire unit (i.e. the meter 10 built into the body 44) can then be installed easily within a pipeline, such as 14.

In FIG. 6, sample gas 20 enters the meter 10 through a sample gas inlet 46 when valve 16 is open. The sample gas inlet 46 is immersed within the pipeline gas 12 flowing through the meter body 44. Since the pipeline gas 12 flowing through the pipeline 14 may be at a high pressure, a diaphragm 47 is used to actuate valve 16. In particular, the diaphragm 47 is located in casing 48 and splits the volume inside the casing 48 into an upper portion 50 and a lower portion 52. When the solenoid valve 57 is open, gas 54 at pipeline pressure flows from within the pipeline 14 (or the meter body 44) through line 56, through regulator 59, into the upper portion 50 of the casing 48. The regulator 59 reduces the gas pressure to about 50 psi. The pressure in the upper portion 50 of the casing 48 pushes on the diaphragm 47 and drives down arm 58 to open valve 16. The opening and closing of the solenoid valve 57 and, thus valve 16 through diaphragm 47 and arm 58, is controlled by electrical signals. Cavity 50 has an atmospheric bleed.

Alternatively, the source of pressure in cavity 50 could be air pressure supplied by an external instrument air supply.

Figure 7:
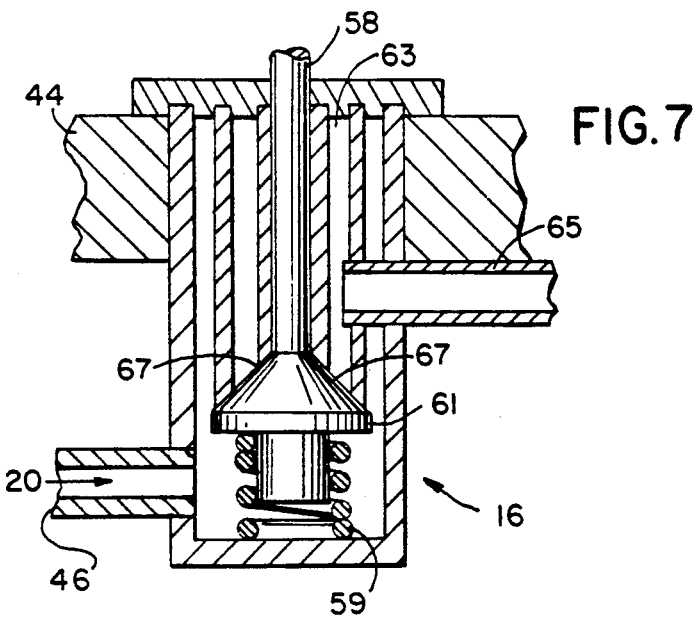
FIG. 7 is a detailed diagram of a preferred embodiment of a first valve of the present invention.

Valve 16 is shown in detail in FIG. 7. When valve 16 is closed, a spring 59 pushes a conical shaped plug 61 into an annular channel 63 to prevent flow through the channel 63. When the solenoid valve 57 is opened and diaphragm 47 drives down arm 58, arm 58 displaces plug 61 downward against the force of the spring 59 and opens valve 16. With the plug 61 displaced downward, sample gas 20 is able to flow into the valve 16 through the annular channel 63 and exit the valve 16 through valve outlet 65 which is in fluid communication with the annular cylinder 63.

When valve 16 is open, sample gas 20 flows into the first chamber 22. In FIG. 6, the first chamber 22 consists mostly of a hollow coil 23 that spirals around the inside perimeter of the meter body 44. The sample gas 20 flows from the first chamber 22 through the mechanical pressure regulator 24. The regulator 24 operates in a normal gas regulator fashion to reduce the sample gas 20 pressure (i.e. a regulator valve (not shown) is positioned by an arm 68 that is displaced by a combination of a spring 60 and a diaphragm 62 within a casing 64.

After flowing through the pressure regulator 24, the sample gas 20 flows to the second chamber 26 if valve 18 is open. In most circumstances, the pressure in line 70 following the pressure regulator 24 is sufficiently low (i.e. 20-30 psig) so that valve 18 can be a solenoid valve rather than a diaphragm driven valve like valve 16.

Figure 8:
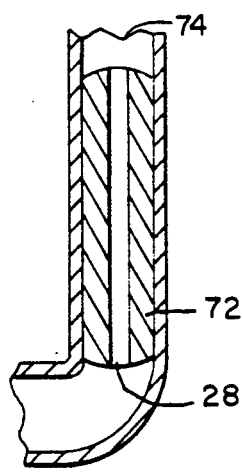
FIG. 8 is a detailed cross-sectional view of a preferred embodiment of a pore/sonic nozzle of the present invention.

After the sample gas 20 flows through the second chamber 26, it flows through the pore 28. The pore 28 is shown in detail in FIG. 8. It is preferred that pore 28 be a 0.002" diameter hole drilled through a piece of sapphire 72. Such a pore 28 can be used to accurately and reliably measure base condition density $\rho_b$ using the invention described in U.S. Pat. No. 4,677,841 and a reference gas apparatus as discussed above. The pore 28 operates to measure the density of sample gas flowing through the pore 28 (as inversely proportional to the square of the mass flow rate of sample gas 20 through the pore 28) when the valve 18 is closed and the meter 10 is operating in the base condition mode. When valve 18 is open and the meter 10 is operating in the flowing condition mode, the pore 28 acts as a sonic nozzle 28 because the ratio of the sample gas pressure applied to the pore 28 (i.e. sonic nozzle 28), which is the regulated pressure in line 70 and the second volume 26, compared to the pressure downstream of the pore 28 (i.e. sonic nozzle 28), which is ambient pressure, is sufficient so that there is constant sample gas mass flow through the pore 28 (i.e. sonic nozzle 28).

After the sample gas 20 flows through the pore 28, it exhausts through opening 74. The exhaust gas can be catalytically burned or returned to the pipeline 14 if desired.

The volume of the first chamber 22 is the volume along the sample gas flow path from the point 67 in the valve 16 where plug 61 meets channel 63 to the point (not shown) in the pressure regulator 24 where the regulator valve reduces the sample gas 20 pressure. Since intake valve 16, the hollow coil 23, and the regulator 24 are immersed within the pipeline gas stream 12, the temperature of the sample gas 20 in the first chamber 22 is maintained at the flow temperature $T_f$ of the pipeline gas 12. Pressure sensor 30 measures the sample gas pressure in the first chamber 22 and temperature sensor 32 measures the temperature in the first chamber 22. Pressure sensor 34 measures sample gas pressure in the second chamber 34. Signals from the temperature sensor 32 and pressure sensors 30 and 34 are sent to the microprocessor 36 to calculate the volume correction ratio $$\left(\frac{\rho_f}{\rho_b}\right)$$

and the flowing condition density $\rho_f$.

SCIENTIFIC AND MATHEMATICAL ANALYSIS

The following analysis is recited to further describe the present invention and to describe the preferred nature of the role of the microprocessor 36. Assuming that the molecular weight (or composition x) and volume of the gas is the same at flowing conditions as at base conditions, the real gas law allows the volume correction ratio $$\frac{\rho_f}{\rho_b}$$

to be written as:

$$\frac{\rho_f}{\rho_b} = \frac{P_f}{P_b} \frac{Z_b}{Z_f} \frac{T_b}{T_f} \quad (1)$$

where the subscript "f" refers to flowing conditions, subscript "b" refers to base conditions, "$\rho$" is gas density, "P" is gas pressure, "Z" is supercompressibility, and "T" is gas temperature. In the present invention, the composition x of the sample gas 20 is the same for conditions at base and for flowing conditions because valve 16 closes and, thus, traps a certain population of sample gas 20 molecules in the first chamber 22. Also, the base condition volume is the same as the flowing condition volume because the volume of the first chamber 22 remains constant.

Therefore, the volume correction ratio $$\left(\frac{\rho_f}{\rho_b}\right)$$

can be determined by measuring three ratios $$\frac{P_b}{P_f}, \frac{T_b}{T_f}, \text{ and } \frac{Z_b}{Z_f}.$$

The base condition temperature $T_b$ and pressure $P_b$ are assigned (e.g. 60° F., 14.7 psia) and need not be measured. The absolute flowing condition temperature $T_f$ and pressure $P_f$ are measured by temperature sensor 32 and pressure sensor 30, respectively. Sensors 30 and 32 measure conditions within the first chamber 22, but the temperature of the sample gas 20 in the first chamber 22 is maintained at $T_f$ and the pressure of the sample gas 20 in the first chamber 22 is preferably $P_f$ at the point in time when valve 16 closes. Note that it would be possible to measure $T_f$ and $P_f$ directly from the pipeline 14, although this is not necessary.

While both T and P measurements seem to form ratios, the transducer constants, or slope calibrations do not cancel because the values of both $P_b$ and $T_b$ are fixed and not measured. Accuracy of pressure sensor 30 and temperature sensor 32 therefore must be maintained.

In order to measure the supercompressibility ratio $$\frac{Z_b}{Z_f},$$

the time rate of change of pressure in the first chamber 22 and the pressure of the sample gas at the sonic nozzle 28 inlet are measured. The following analysis explains in detail the preferred way of determining the supercompressibility ratio $$\frac{Z_b}{Z_f}.$$

The time rate of change of pressure in a volume with gas flowing therefrom at a mass flowrate $\omega$ is:

$$\frac{\partial P}{\partial t} = \left(\frac{RT}{MV}\right) \frac{Z^2 \omega}{[1 - c(T,x)P^2]} \quad (2)$$

where $c(T,x)$ is a third virial pressure coefficient which is a function of temperature T and composition x, and Z is a supercompressibility factor which can be represented by the pressure virial series: $Z(T,x) = 1 + b(T,x)P + c(T,x)P^2$; where $b(T,x)$ is a second virial pressure coefficient and also a function of temperature T and composition x. In the gas density meter 10 as shown in FIGS. 1 and 6, the volume V appearing in Eq. (2) is the volume of the first chamber 22. Since the first chamber 22 is immersed in the pipeline gas stream 12, the sample gas temperature T in the first volume is the pipeline flow condition temperature $T_f$ and can be considered to be constant for one measurement cycle which is the period between successive closings of valve 16 intended to be about 30 to 60 seconds. Also, the composition x of sample gas 20 in the first chamber 22 is constant over a measurement cycle because of the above described trapping by closing valve 16.

Figure 3:
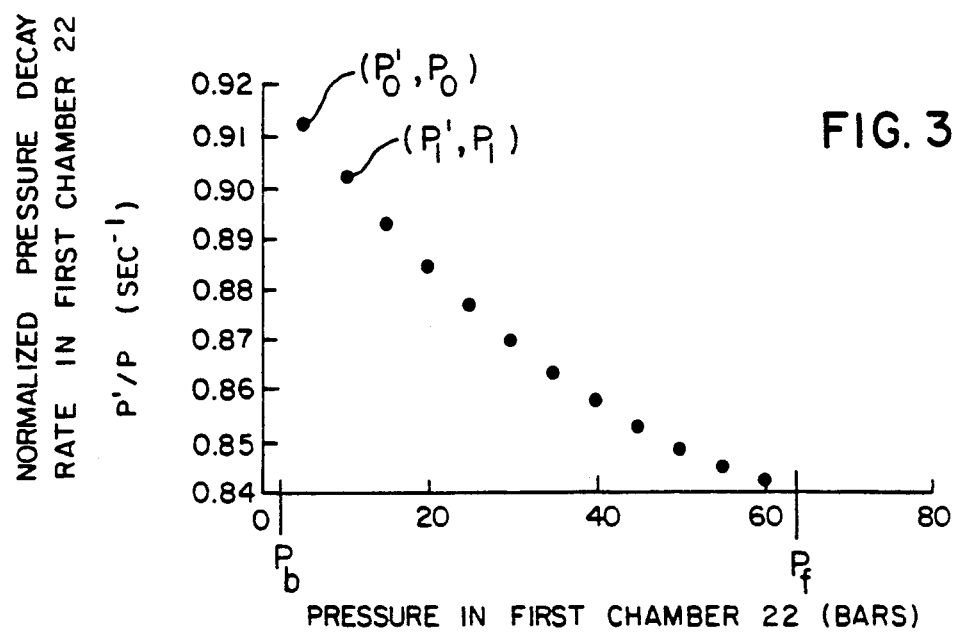
FIG. 3 is a plot of the normalized rate of change of pressure in the first chamber as a function of absolute pressure in the first chamber when the present invention as shown in FIG. 1 is operating.

The invention measures the rate of change of pressure as described in Eq. (2) at several pressures as the pressure in the first chamber 22 decays over a measurement cycle. Referring to FIG. 3, these several pressures include pressures approaching the flowing condition pressure $P_f$ and the base condition pressure $P_b$.

Since the quantity (MV/RT) is constant as pressure in the first chamber 22 decays over a single measurement cycle, (i.e. the sample gas 20 in the first chamber has constant molecular weight M, temperature T, and is within the same volume V), Eq. (2) can be solved at two different pressures $P_1$ and $P_2$.

$$\frac{\omega_1 Z_1^2(T_f,x_f)}{P_1[1 - c(T_f,x_f)P_1^2]} = \frac{\omega_2 Z_2^2(T_f,x_f)}{P_2[1 - c(T_f,x_f)P_2^2]} \quad (3)$$

where P' represents $$\frac{dP}{dt}.$$

Note both sides of Eq. (3) are expressed in terms of the flowing temperature $T_f$. This is because the design condition whereby the sample gas 20 in the first chamber 22 is held at the flowing temperature $T_f$ when the meter 10 is operating in flowing condition mode. This apparent error in measurement conditions is accounted for by a temperature transfer $$\left[\frac{Z_2^2(T_f,x_f)}{Z_2^2(T_b,x_f)}\right].$$

Solving Eq. (3) for $Z_1/Z_2$ yields:

$$\frac{Z_1^2(T_f,x_f)}{Z_2^2(T_f,x_f)} = \left(\frac{\omega_2}{\omega_1}\right)\left(\frac{P_1}{P_2}\right)\left[\frac{1 - c(T_f,x_f)P_1^2}{1 - c(T_f,x_f)P_2^2}\right] \quad (4)$$

Multiplying each side of Eq. (4) by the temperature transfer term $$\left[\frac{Z_2^2(T_f,x_f)}{Z_2^2(T_b,x_f)}\right]$$

results in:

$$\frac{Z_1^2(T_f,x_f)}{Z_2^2(T_b,x_f)} = \quad (5)$$

$$\left[\frac{Z_2^2(T_f,x_f)}{Z_2^2(T_b,x_f)}\right]\left(\frac{\omega_2}{\omega_1}\right)\left[\frac{1 - c(T_f,x_f)P_1^2}{1 - c(T_f,x_f)P_2^2}\right]\left(\frac{P_1}{P_2}\right)$$

Substituting Eq. (5) into Eq. (1) and designating $P_1$ as $P_f$ and $P_2$ as $P_b$ provides the volume correction ratio $$\frac{P_f}{P_b}:$$

$$\frac{\rho_f}{\rho_b} = \left(\frac{P_f}{P_b}\right)\left(\frac{T_b}{T_f}\right)\left(\frac{P_b}{P_f}\right)^{\frac{1}{2}}\left(\frac{\omega_f}{\omega_b}\right)^{\frac{1}{2}}\left[\frac{Z_b(T_b,x_f)}{Z_b(T_f,x_f)}\right]^{\frac{1}{2}}\left[\frac{1 - c(T_f,x_f)P_b^2}{1 - c(T_f,x_f)P_f^2}\right]^{\frac{1}{2}} \quad (6)$$

Since the base condition pressure $P_b$ is usually close to 1 Bar and "c(T_f,x_f)" is usually small ($\approx 3 \times 10^{-6}$ Bar$^{-2}$), Eq. (6) can be further modified to:

$$\frac{\rho_f}{\rho_b} = \left(\frac{P_f}{P_b}\right)\left(\frac{T_b}{T_f}\right)\left(\frac{P_b}{P_f}\right)^{\frac{1}{2}}\left(\frac{\omega_f}{\omega_b}\right)^{\frac{1}{2}}\left[\frac{Z_b(T_b,x_f)}{Z_b(T_f,x_f)}\right]^{\frac{1}{2}}\left[\frac{2}{2 - c(T_f,x_f)P_f^2}\right] \quad (7)$$

The temperature transfer term $$\left[\frac{Z_b(T_b,x_f)}{Z_b(T_f,x_f)}\right]^{\frac{1}{2}}$$

can be stated in terms of the virial series as:

$$\frac{Z_b(T_b,x_f)}{Z_b(T_f,x_f)} = \frac{1 + b(T_b,x_f)P_b + c(T_b,x_f)P_b^2}{1 + b(T_f,x_f)P_b + c(T_f,x_f)P_b^2} \quad (8)$$

Since the product $c(T,x) P_b$ is very small, Eq. (8) may be written as:

$$\frac{Z_b(T_b,x_f)}{Z_b(T_f,x_f)} = 1 + [b(T_b,x_f) - b(T_f,x_f)]P_b \quad (9)$$

Substituting Eq. (9) into Eq. (7) results in:

$$\frac{\rho_f}{\rho_b} = \left(\frac{P_f}{P_b}\right)\left(\frac{T_b}{T_f}\right)\left(\frac{P_b}{P_f}\right)^{\frac{1}{2}}\left(\frac{\omega_f}{\omega_b}\right)^{\frac{1}{2}}\{ + \quad (10)$$

$$[b(T_b,x_f) - b(T_f,x_f)]P_b\}\left[\frac{2}{2 - c(T_f,x_f)P_f^2}\right]$$

Equation (10) now becomes the basis for measuring the volume correction ratio $$\frac{P_f}{P_b}.$$

The last term in Eq. (10) involving the third virial coefficient "c" is nearly unity. The average value of "c" is about $3 \times 10^{-6}$ Bar$^{-2}$. Using this value for "c", the flowing condition pressure $P_f$ can reach a maximum of 55 Bar and the error associated with approximately the last term as unity will be less than 0.5%. Alternatively, an average value of "c" can be adopted as a compensating constant, and the maximum pressure $P_f$ limit can be raised to about 85 Bar for 0.5% accuracy. In addition, as will be shown later, it may be possible to calculate the value "c" to further raise the maximum operating pressure $P_f$ (See Eqs. 22–26).

The term $1 + [b(T_b,x) - b(T_f,x)] P_b$ in Eq. (10) is also nearly unity for gas flowing at near ambient conditions and can be ignored. For example, the value of "b" (the second virial pressure coefficient) is generally about $2 \times 10^{-3}$ because natural gases are composed mostly of methane. The value of "b" varies with temperature, but the variation is small about 40 PPM/°C. for natural gases. Natural gas pipelines usually operate at 40° F. to 100° F. (i.e., 4° C. to 38° C.), and $P_b$ is typically about 1

Bar. Thus, for natural gas pipelines, the maximum temperature difference $(T_b - T_f)$ should be about $\pm 10°$ C. so the maximum expected variation in the term $1 + [b(T_b x) - (T_f, x)] P_b$ is about $\pm 0.02$ to $0.04\%$.

The term $$\left(\frac{\omega_f}{\omega_b}\right)^{\frac{1}{2}}$$

in Eq. (10) must be determined by either measuring the mass flow rates, $\omega_f$ for flowing conditions and $\omega_b$ for base conditions; or holding the rates $\omega_f$ or $\omega_b$ constant. If the mass flowrate through the sonic nozzle 28 (i.e., pore 28) is held constant, the ratio of mass flowrates $$\left(\frac{\omega_f}{\omega_b}\right)^{\frac{1}{2}}$$

is unity. This can happen, however, only if pressure regulator 24 is perfect. But, most pressure regulators cannot maintain perfect output pressure when inlet pressure varies. In the real world, where mass flowrate through the sonic nozzle 28 is not constant due to real regulator conditions, the mass flowrate ratio $$\left(\frac{\omega_f}{\omega_b}\right)^{\frac{1}{2}}$$

is measured. This measurement or correction for changes in mass flowrate during a measurement cycle can be done by measuring the sonic nozzle 28 inlet pressure using a pressure transducer 34 to measure the pressure in the second chamber 26. The following analysis explains this method of measuring the mass flowrate ratio $$\left(\frac{\omega_f}{\omega_b}\right)^{\frac{1}{2}}.$$

The sonic velocity of a fluid $v$ can be accurately represented as:

$$v^2 = \left(\frac{dP}{d\rho}\right)_s \quad (11)$$

where $P$ is absolute pressure, $\rho$ is density, and the process operates at constant entropy $s$. For an ideal gas:

$$\left(\frac{P}{\gamma^k}\right) = \text{constant} \quad (12)$$

where $\gamma$ is the weight density and $k$ is the specific heat ratio. Combining Eqs. (11) and (12) for an ideal gas gives:

$$v = \sqrt{k g_c R T} \quad (13)$$

where $R$ is the universal gas constant, $T$ is the absolute temperature and $g_c$ is the gravity constant. The ideal gas equation (i.e., Eq. (13)) is independent of pressure.

If supercompressibility exists (i.e., the gas is not ideal), the relation in Eq. (13) is not accurate. But Eq. (13) can be modified for non-ideal gases to an equation of the form:

$$v = \sqrt{k_s g_c Z R T} \quad (14)$$

where $k_s$ is an isentropic exponent. Note that Z is a function of pressure. As taught by "Physical Properties of Natural Gases," N.V. Nederlandse Gasunie, page 107, a formula similar to Eq. (14)

$$(\text{i.e. } \sqrt{1000 k Z R T / M})$$

is given, and this reference indicates that the formula is applicable to a non-ideal gas. In Eq. (14), the isentropic constant $k_s$ is a number which forces the P-v relation to accurately approximate the local real gas relation for a small isentropic expansion or compression. The constant $k_s$ is not a thermodynamic property and should not be associated with the specific heat ratio for real gases, although comparing Eq. (13) to Eq. (14) shows that $k_s = k$ for ideal gases (i.e. $Z = 1$). At most, $k_s$ seems to be inversely proportional molecular weight M (note the Gasunie representation $$\sqrt{1000 k Z R T / M}).$$

Figure 9:
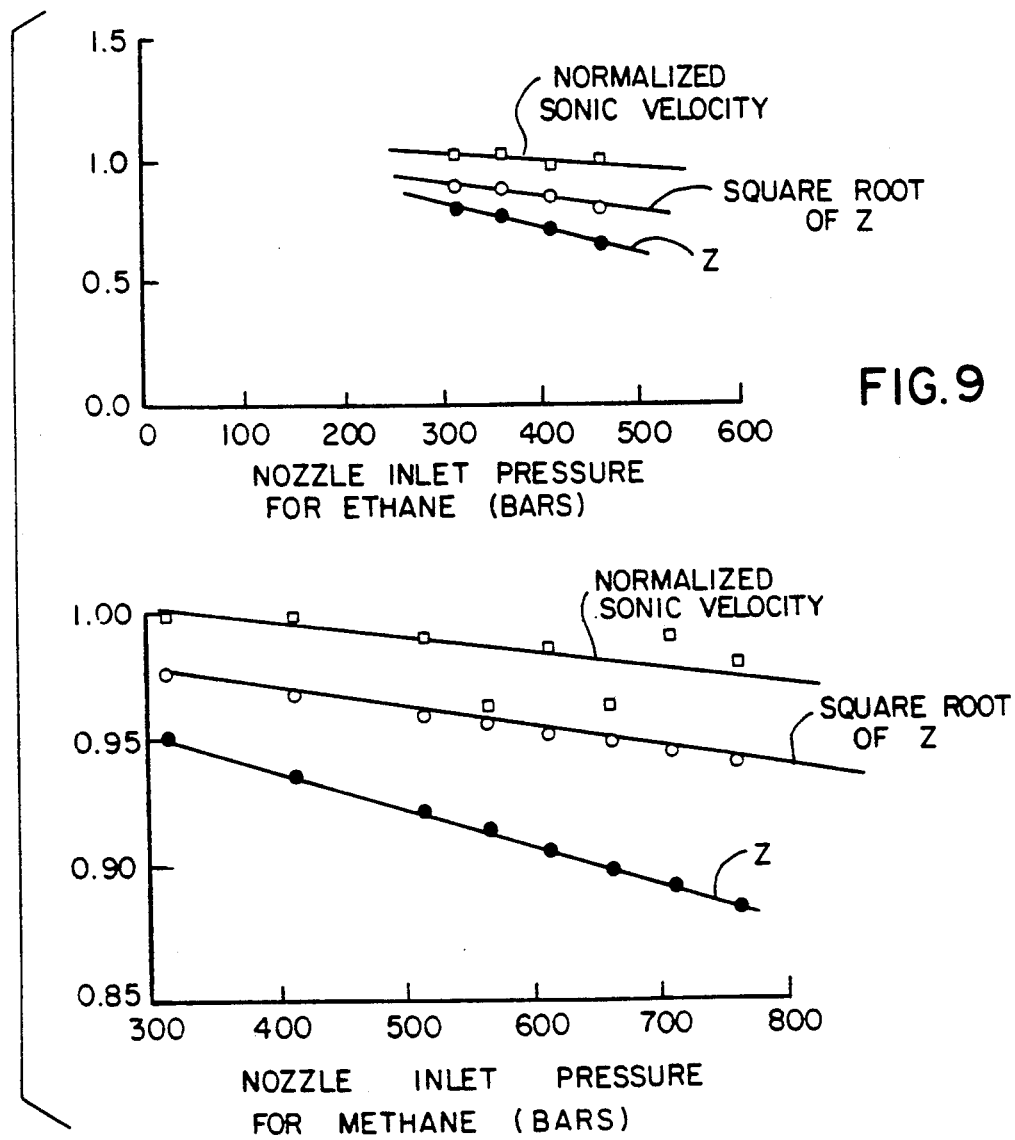
FIG. 9 shows plots of experimental data for ethane gas and methane gas that relates to a preferred embodiment of the present invention.

Experimental testing has confirmed Eq. (14). The testing was carried out on a pore of the same type as pore 28 (i.e. sonic nozzle 28) but at higher inlet pressures than is preferred in the present invention. Sonic flow through the pore (i.e. sonic nozzle) was, therefore, present. The testing was done for three gases: nitrogen, methane, and ethane. Ethane exhibited the largest Z effects. The actual sonic velocity at the pore inlet for both ethane and methane have been calculated and the results confirm Eq. (14). Refer in particular to FIG. 9 in which normalized sonic velocity through the pore was plotted versus pressure, along with Z and $Z^{\frac{1}{2}}$ for both methane and ethane. From FIG. 9, it is easy to see that normalized velocity data parallels $Z^{\frac{1}{2}}$, not Z; and this confirms Eq. (14).

Using Eq. (14), the mass flowrate $\omega_N$ of sample gas 20 exiting the nozzle 28 (i.e., pore 28), under critical pressure conditions, can be stated as:

$$\omega_N = v_I A_N \rho_I = A_N P_I M_I \left(\frac{k_s g_c}{Z_I R T_I}\right)^{\frac{1}{2}} \quad (15)$$

where the subscript "N" indicates a nozzle mechanical condition, "I" represents a dynamic inlet condition, and $A_N$ is the cross-sectional area of the sonic nozzle 28. As used herein, the term critical flow means a condition where the ratio of pressure upstream from the sonic nozzle 28 compared to the pressure downstream of the sonic nozzle 28 is sufficient so that the relations in Eqs. (14) and (15) for non-ideal gases are substantially accurate.

The mass flowrate ratio $$\left(\frac{\omega_1}{\omega_2}\right)$$

for two states, where pressure in the first chamber 26 is $P_1$ or $P_2$, can be represented as:

$$\frac{\omega_1}{\omega_2} = \frac{Z_{I,2}^{\frac{1}{2}} P_{I,1}}{Z_{I,1}^{\frac{1}{2}} P_{I,2}} \tag{16}$$

Referring to Eqs. (15) and (16), the temperature ratio $$\left(\frac{T_{I,2}}{T_{I,1}}\right)$$

is nearly constant over a single measurement cycle (due to the heat sinking of the assembly) and the ratio $$\left(\frac{T_{I,b}}{T_{I,f}}\right)^{\frac{1}{2}}$$

can therefore be ignored.

Since the sonic nozzle inlet pressure is relatively low (~30 psig), the supercompressibility Z in Eq. (16) can be represented as a truncated virial pressure series:

$$Z = 1 + bP \text{ and } \sqrt{Z} = 1 + \frac{b}{2}P \tag{17}$$

Due to the small nature of "b", the supercompressibility ratio in Eq. (16) can be represented by:

$$\sqrt{\frac{Z_{I,2}}{Z_{I,1}}} = 1 + \frac{b}{2}(P_{I,2} - P_{I,1}) \tag{18}$$

Equation (18) shows that the low pressure operating conditions at the inlet of the sonic nozzle 28 (i.e., pore 28) are accompanied by supercompressibility effects too small to be of concern when determining the mass flowrate ratio $$\left(\frac{\omega_1}{\omega_2}\right).$$

In Eq. (18), the value of the second virial pressure coefficient "b" is about 0.002 Bar$^{-1}$ and the expected variation of the sonic nozzle inlet pressure is about $\frac{1}{3}$ Bar. Thus, the second term in Eq. (19) can be expected to vary about 0.03% and can be neglected. This means that the mass flowrate ratio $$\left(\frac{\omega_1}{\omega_2}\right)$$

in Eq. (16) can be determined by measuring, only the absolute pressure at the sonic nozzle 28 inlet. The mass flow ratio $$\left(\frac{\omega_1}{\omega_2}\right)$$

in Eq. (16) can be represented as:

$$\frac{\omega_1}{\omega_2} = \frac{P_{I,1}}{P_{I,2}} \tag{19}$$

Equation (10) can now be rewritten as:

$$\frac{\rho_f}{\rho_b} = \left(\frac{P_f}{P_b}\right)\left(\frac{T_b}{T_f}\right)\left(\frac{P_f}{P_b}\right)^{\frac{1}{2}}\left(\frac{P_{I,f}}{P_{I,b}}\right)^{\frac{1}{2}}\left[\frac{2}{2 - c(T_f, x_f)P_f^2}\right] \tag{20}$$

where $$\left(\frac{P_{I,f}}{P_{I,b}}\right)^{\frac{1}{2}}$$

is substituted for $$\left(\frac{\omega_1}{\omega_2}\right)$$

and the term $\{1 + [b(T_b, x_f) - b(T_f, x_f)]P_b\}$ is ignored. To solve Eq. (20), the pressure decay rate ratio $$\left(\frac{P_b'}{P_f'}\right)^{\frac{1}{2}}$$

must be determined. The following discussion explains the determination of the pressure decay rate ratio $$\left(\frac{P_b'}{P_f'}\right)^{\frac{1}{2}}.$$

Figure 2:
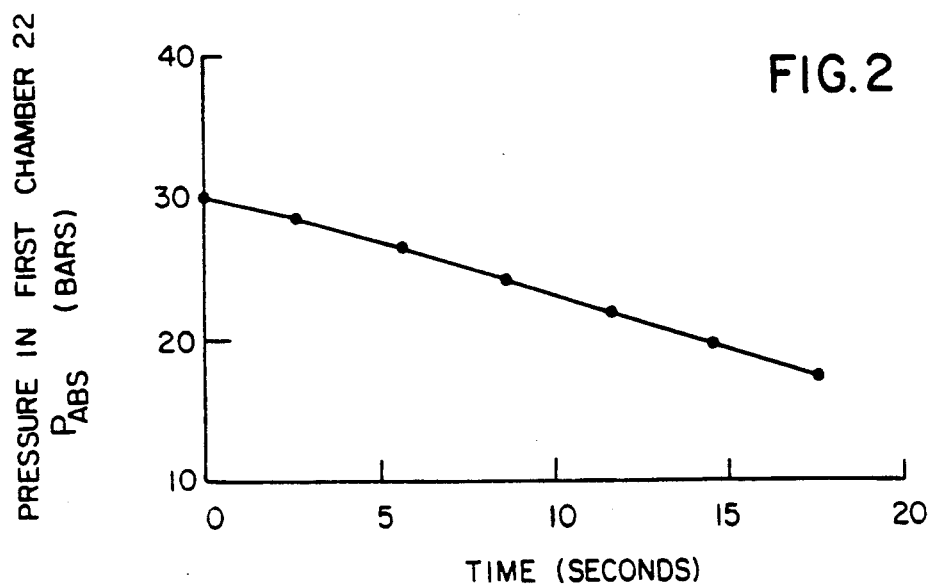
FIG. 2 is a plot of the pressure in a first fixed-volume chamber as a function of time when the present invention as shown in FIG. 1 is operating.

FIGS. 2 and 3 are the results of a computer simulation. FIG. 2 represents a typical plot of pressure in the first chamber 22 as it decays over a measurement cycle. The pressure transducer 30 that senses the pressure in the first chamber 22 should have sufficient bandwidth to accurately measure the pressure in the first chamber 22 throughout the entire measurement cycle. The microprocessor 36 records several pressure measurements from transducer 30 as the pressure decays and the time that each pressure measurement occurs. The time rate of change of the pressure in the first chamber 22 (i.e. P') can then be computed for several pressures during the measurement cycle. FIG. 3 shows the variation in P' versus pressure in the first chamber 22. The curvature of P' is due to supercompressibility of the gas.

The value of P' at flowing conditions $P_f$ and at base conditions $P_b$ cannot be measured directly without additional apparatus. To directly measure P' at $P_f$ would require an initial or starting pressure in the first chamber 22 that is higher than the pipeline gas 12 pressure because the P' measurement should be centered about the pipeline gas 12 pressure $P_f$. For the same reason, directly measuring $P'_b$ would probably require exhausting the first chamber 22 into a partial vacuum. Direct measurement of $P'_b$ and $P'_f$ does not therefore seem practical.

However, intermediate P' values can be measured accurately. Numeric methods can then be used to obtain accurate values of $P'_f$ and $P'_b$. For example, considering the two left most data points in FIG. 3, ($P_o$,$P'_o$) and $P_1$, $P'_1$), the time rate of change of pressure at the base condition is:

$$P'_b = \left[ \frac{(P_b - P_1)P'_0 - (P_b - P_0)P'_1}{(P_1 - P_0)} \right] \tag{21}$$

A similar expression for $P'_f$ also exists. One condition on the accuracy of Eq. (21) is that the function $$\frac{P'}{P}$$

be relatively linear in the region local to $P_b$ (or $P_f$ if determining $P'_f$). FIG. 3 shows that the rate of change of pressure P' with pressure or time is a slowly varying function, so Eq. (21) is accurate for interpolation.

Measurement of pressure decay rates P' required to solve Eq. (21) for $P'_b$ and $P'_f$ can be accomplished in several fashions. The preferred method is to divide the time between two pressure measurements $\Delta t$ into the difference of the measured pressures $\Delta P$ to obtain values of P' and then use Eq. (21) to interpolate the values of $P'_b$ and $P'_f$. This method has the advantage of stability and has good resolution because time measurement resolution is very good.

Another method is to record the absolute pressures in a time series (i.e. record the pressure in the first chamber 22 vs. time as in FIG. 2). Numeric differentiation methods can then be applied to transform the pressure time series into normalized P' versus P data as in FIG. 3. The numeric differentiation process can be carried out using Newton's formulas for data spaced equally in time, or using LaGrange's formula for data spaced unequally in time. If numeric differentiation is used, it is preferred that a large number of points be employed because numeric differentiation can be a noise amplifying process.

Analogue differentiation using operational amplifier techniques could also be used to measure P', but the relatively slow nature of the measurement cycle would be a severe complication.

Another method for measuring the supercompressibility ratio $$\left( \frac{Z_b}{Z_f} \right)$$

in Eq. (1) is to compute the virial coefficients of the gas from pressure data or from the derivative of the pressure data; and, then compute the ratio $$\left( \frac{Z_b}{Z_f} \right)$$

using the computed virial coefficients (i.e. $Z=1+bP+cP^2$). The value of a single pressure decay rate "n" in a series of pressure decay rate measurements can be described as:

$$P_n \left( \frac{MV}{RT} \right)_n = \frac{Z_n^2 \omega_n}{(1 - cP_n^2)} \tag{22}$$

where the dependence of Z and c on temperature and composition can be ignored because of the constant composition and relatively constant temperature environment in the first chamber 22. The measured value at another point "n+1" is:

$$P_{n+1} \left( \frac{MV}{RT} \right)_{n+1} = \frac{Z_{n+1}^2 \omega_{n+1}}{(1 - cP_{n+1}^2)} \tag{23}$$

Since Z can be represented by a virial series as $Z=1+bP+cP^2$, $Z^2/(1-cP^2)=1+2b\ P+(3c+b^2)P^2$. Therefore, in light of Eq. (19), dividing Eq. (22) by (23) results in:

$$\left( \frac{P_n}{P_{n+1}} \right)\left( \frac{P_{I,n+1}}{P_{I,n}} \right) - 1 = \tag{24}$$

$$2b(P_n - P_{n+1}) + (3c + b^2)(P_n^2 - P_{n+1}^2)$$

because $T_n=T_{n+1}$ due to the relatively constant temperature in the first chamber 22, $M_n=M_{n+1}$ due to trapping (i.e. valve 22 is closed), and $V_n=V_{n+1}$ due to the fixed volume of chamber 22.

With another set of pressure measurements, the following similar relation can be formed:

$$\left( \frac{P_{n+1}}{P_{n+2}} \right)\left( \frac{P_{I,n+2}}{P_{I,n+1}} \right) - 1 = \tag{25}$$

$$2b(P_{n+1} - P_{n+2}) + (3c + b^2)(P_{n+1}^2 - P_{n+2}^2)$$

And, with a third set of pressure measurements, the following relation:

$$\left( \frac{P_{n+2}}{P_{n+3}} \right)\left( \frac{P_{I,n+3}}{P_{I,n+2}} \right) - 1 = \tag{26}$$

$$2b(P_{n+2} - P_{n+3}) + (3c + b^2)(P_{n+2}^2 - P_{n+3}^2)$$

Therefore, by making pressure measurements in the first chamber 22 with pressure sensor 30 (i.e. $P_n$, $P_{n+1}$, etc.) and in the second chamber 26 with pressure sensor 34 (i.e. $P_{I,n}$; $P_{I,n+1}$; etc.) at a multiplicity of points throughout the measurement cycle, values for "b" and "c" can be computed. Note that it might be statistically advantageous to solve for "b" and "$(3c+b^2)$" and then compute "c". Values $Z_b$ and $Z_f$ can be computed from a virial expansion using these values of "b" and "c", and known $P_b$ or measured $P_f$, respectively. (Note that this method of determining the virial coefficients may also be used to reduce errors associated with the last term $$\left[ \frac{2}{2 - c(T_f,x_f)P_f^2} \right]$$

in Eq. (10) at high operating pressures $P_f$.)

OPERATION WITH A VOLUMETRIC FLOWMETER

Figure 4:
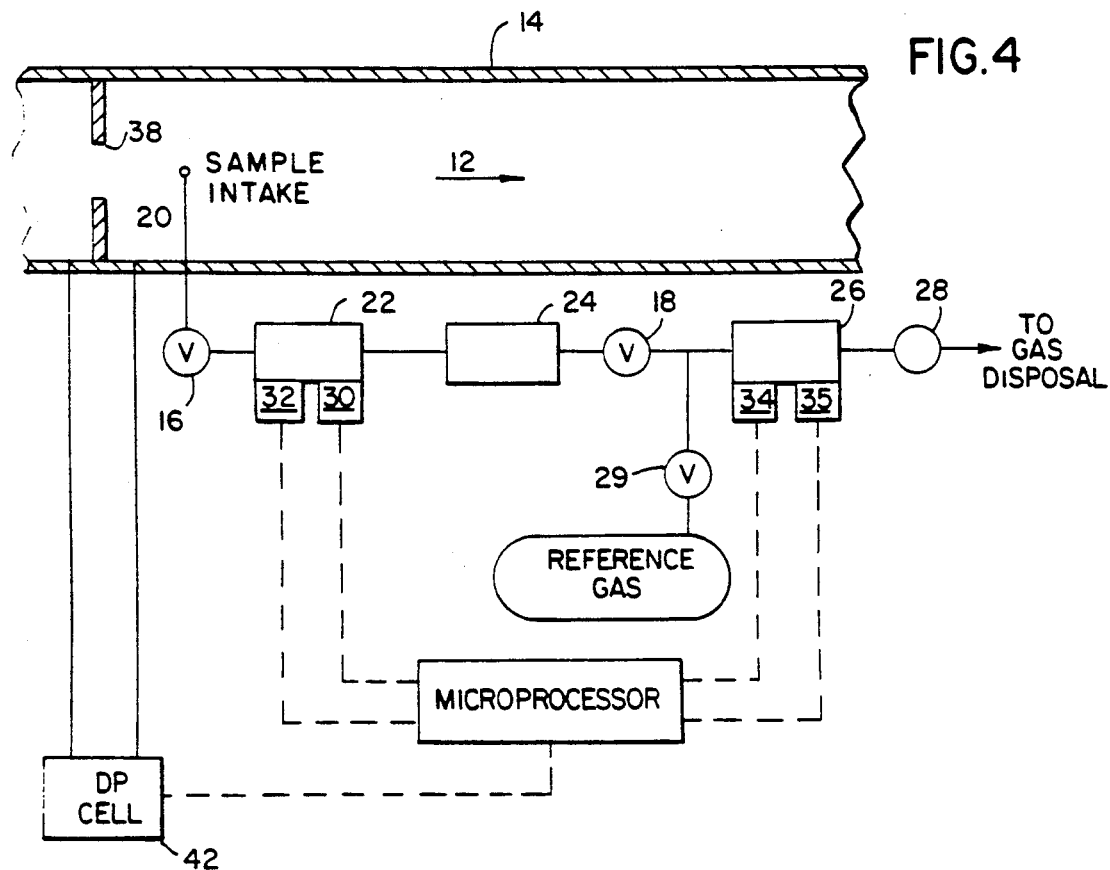
FIG. 4 is a schematic drawing of the preferred way of using a differential pressure volumetric flowmeter with the present invention as shown in FIG. 1.
Figure 5:
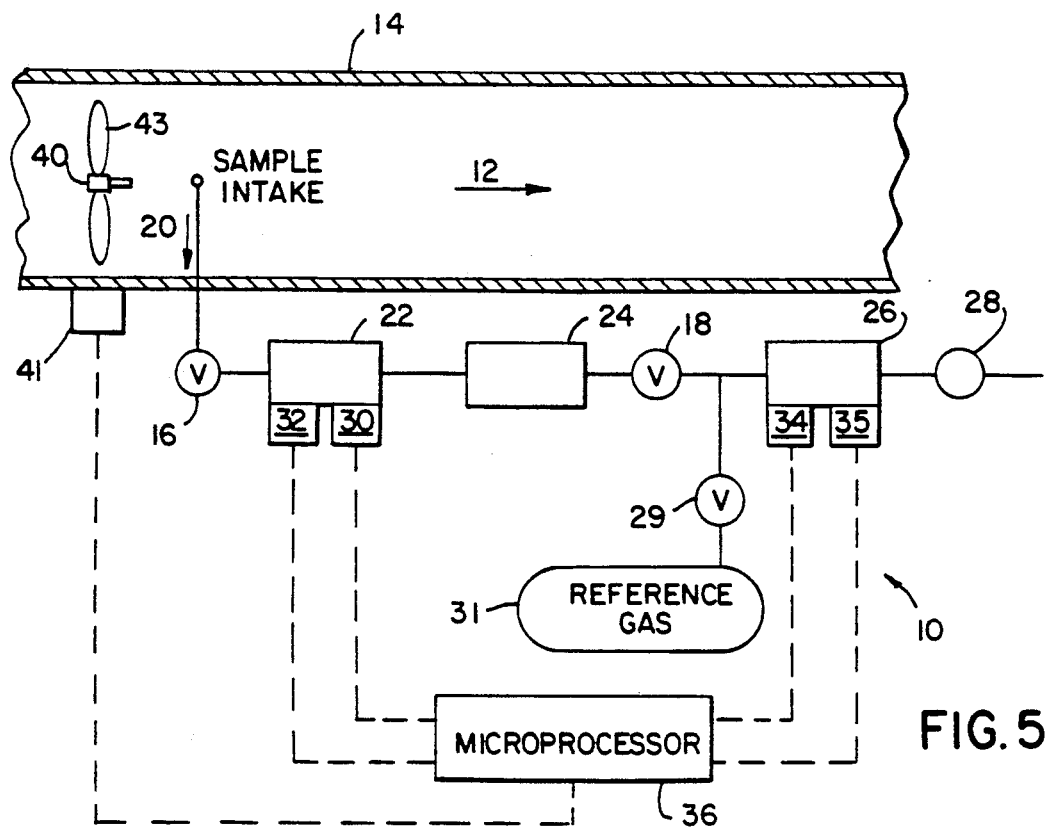
FIG. 5 is a schematic drawing of the preferred way of using a linear volumetric flowmeter with the present invention.

Referring to FIGS. 4 and 5, the invention can be used to determine a base condition volumetric flowrate $Q_b$ of the pipeline gas 12 flowing through the pipeline 14 from a flowing condition volumetric flowrate $Q_f$ measured by a volumetric flowmeter (e.g. 38 in FIG. 4 and 40 in FIG. 5):

$$Q_b = \left(\frac{\rho_f}{\rho_b}\right) Q_f \tag{27}$$

In FIGS. 4 and 5, flow of sample gas 20 and reference gas is shown by solid lines and electrical connections are shown by dashed lines. Referring in particular to FIG. 4, flow of pipeline gas 12 through an orifice plate 38 produces a pressure drop $\Delta P_f$ and a DP cell 42 measures the pressure drop $\Delta P_f$. A signal from the DP cell 42 representing $\Delta P_f$ is sent to the microprocessor 36 to determine the mass flowrate $\omega_f$ of the pipeline gas 12 through the pipeline 14. The mass flowrate $\omega_f$ through the orifice plate 38 (i.e. through the pipeline 14) is described by the orifice equation:

$$\omega_f = K C_{Df} Y_f \sqrt{\rho_f \Delta P_f} \tag{28}$$

where the values of $\rho_f$ is calculated within the microprocessor 36 from previously gathered data; $Y_f$ is the upstream expansion factor that accounts for changes in pressure as the pipeline gas 12 flows through the orifice 38 (e.g. AGA-3 standard); and $C_{Df}$ and K are known constants for the orifice plate 38. The microprocessor 36 can then determine the flowing condition flowrate $Q_f$ for a differential pressure meter by:

$$Q_f = \frac{\omega_f}{\rho_f} = K C_{Df} Y_f \sqrt{\frac{\Delta P_f}{\rho_f}} \tag{29}$$

and the base condition flowrate $Q_b$ by:

$$Q_b = \frac{\omega_f}{\rho_b} = \frac{K C_{Df} Y_f}{\rho_b} \sqrt{\rho_f \Delta P_f} \tag{30}$$

FIG. 5 shows operation of the invention with a linear volumetric flowmeter, such as a turbine meter, a vortex, or any other meter with an output signal linearly proportional to the volumetric flow of the gas 12 through the pipeline. If a turbine meter 40 is used as shown in FIG. 5, the flowing condition volumetric flow rate $Q_f$ is given by the calibration equation:

$$Q_f = \frac{f_t}{K_t} \tag{31}$$

where $f_t$ is the frequency of rotation and $K_t$ is a scaling constant. The frequency of rotation $f_t$ is detected by a frequency detector 41 located on the outer surface of pipeline 14 near impeller 43 of the turbine meter 40. The signal from the frequency detector 41 is then relayed to the microprocessor, along with the data used to determine the volume correction ratio $$\frac{\rho_f}{\rho_b}.$$

The microprocessor 36 then calculates the base volumetric flowrate by:

$$Q_b = \frac{\rho_f}{\rho_b} \frac{f_f}{K_f} \tag{32}$$

Many modifications and variations of the preferred embodiment that are within the spirit and scope of the invention will be apparent to those with ordinary skill in the art.

I claim:

1. A volume corrector comprising:
   means for tapping sample gas from a pipeline through which pipeline gas flows at a flowing temperature and pressure in contrast to a base temperature and pressure;
   a first chamber of fixed volume for receiving sample gas tapped from the pipeline, the sample gas being maintained at substantially the same temperature as the pipeline gas flowing temperature when contained in the first chamber;
   a first pressure sensor for measuring the pressure of the sample gas in the first chamber;
   a first temperature sensor for measuring the pipeline gas flowing temperature which is substantially the same as the temperature of the sample gas in the first chamber;
   a first valve for controlling the flow of sample gas to the first chamber;
   a flow restrictor located downstream of the first chamber through which sample gas flowing from the first chamber flows;
   a pressure regulator located downstream of the first chamber and upstream of the flow restrictor for reducing the pressure of sample gas flowing from the first chamber before it flows to the flow restrictor so that flow from the first chamber through the flow restrictor is maintained at a substantially constant rate; and
   a controller for receiving signals from the first pressure sensor and the temperature sensor and for determining a ratio $$\frac{\rho_f}{\rho_b}$$

of a density of the pipeline gas at the flowing temperature and pressure compared to a density of the pipeline gas at the base temperature and pressure.

2. A volume corrector as recited in claim 1 wherein the flow restrictor is a sonic nozzle having an inlet and the pressure regulator reduces the pressure of the sample gas flowing from the first chamber to a pressure that is sufficient to maintain critical flow through the sonic nozzle.

3. A volume corrector as recited in claim 2 further comprising:
   a second pressure sensor for measuring the pressure of the sample gas at the sonic nozzle inlet; and
   wherein the controller further receives a signal from the second pressure sensor.

4. A gas density meter as recited in claim 1 wherein the pressure regulator reduces the pressure of the sample gas flowing from the first chamber to a pressure that is sufficient to maintain critical flow through the flow restrictor when the second valve is open.

5. A method for determining a ratio $$\frac{p_f}{p_b}$$

of a density $p_f$ of a pipeline gas in a pipeline at a flowing temperature and pressure compared to a density $p_b$ of the pipeline gas at a base temperature and pressure, the method comprising:

flowing sample gas tapped from the pipeline to a first chamber of fixed volume, the sample gas being maintained at substantially the same temperature as the pipeline gas flowing temperature when contained in the first chamber;

measuring the pressure of the sample gas in the first chamber;

measuring the temperature of the sample gas in the first chamber which is substantially the same as the pipeline gas flowing temperature;

stopping the flow of sample gas to the first chamber when the pressure in the first chamber reaches the pipeline gas flow pressure;

flowing sample gas from the first chamber at a substantially constant mass flowrate;

determining the time rate of change of the pressure in the first chamber; and deriving the ratio $$\frac{p_f}{p_b}$$

from the time rate of change of pressure in the first chamber and the flowing temperature and pressure.

6. A method as recited in claim 5, wherein sample gas is flowed from the first chamber at a substantially constant mass flowrate by:

flowing sample gas from the first chamber to a sonic nozzle at a sample gas pressure sufficient to maintain critical flow through the sonic nozzle;

7. A method as recited in claim 6 further comprising the steps of:

measuring the pressure of the sample gas at the inlet to the sonic nozzle; and correcting for variations in the sample gas mass flowrate from the first chamber.

8. A method for determining a flowing condition density $p_f$ of a pipeline gas flowing through a pipeline at a flowing temperature and pressure, the method comprising:

measuring a base condition density $p_b$ of the pipeline gas;

flowing sample gas tapped from the pipeline to a first chamber of fixed volume until the pressure in the first chamber reaches the pipeline gas flowing pressure, the sample gas being maintained at substantially the same temperature as the pipeline gas flowing temperature when contained in the first chamber;

measuring the pressure of the sample gas in the first chamber;

measuring the temperature of the sample gas in the first chamber which is substantially the same as the pipeline gas flow temperature;

stopping the flow of sample gas to the first chamber and flowing the sample gas from the first chamber at a substantially constant mass flowrate;

measuring the time rate of change of the pressure in the first chamber, deriving the flowing condition density $p_f$ of the pipeline gas from the flowing temperature and pressure, the time rate of change of pressure in the first chamber, and the base condition density $p_b$.

9. A method as recited in claim 8 wherein sample gas is flowed from the first chamber at a substantially constant mass flowrate by flowing sample gas from the first chamber to a sonic nozzle at a sample gas pressure sufficient to maintain critical flow through the sonic nozzle.

10. A method as recited in claim 9 further comprising the steps of: measuring the pressure of the sample gas at the inlet to the sonic nozzle; and correcting for variations in the sample gas mass flowrate from the first chamber.

11. A method as recited in claim 8 wherein the base condition density $p_b$ of the pipeline gas is measured by:

flowing sample gas to the first chamber and allowing the sample gas to flow through into a second chamber;

stopping the flow of sample gas into the second chamber;

flowing sample gas from the second chamber through a pore, the pore being sized so that the square of the sample gas mass flow rate through the pore is inversely proportional to the density of the sample gas flowing through the pore;

measuring the time rate of change of the pressure in the second chamber as sample gas flows through the pore;

deriving a pore density of the sample gas as proportional to the inverse of the square of the time rate of change of pressure in the second chamber; and comparing the pore density to the density of a reference gas measured in a like manner.

12. A flowmeter that determines a base condition volumetric flow rate $Q_b$ of a gas flowing through a pipeline which corresponds to a volumetric flow rate at a base temperature and pressure comprising:

a volumetric flowmeter for measuring a flowing condition volumetric flow rate of the pipeline gas $Q_f$ flowing through the pipeline at a flowing temperature and pressure;

means for tapping sample gas from the pipeline;

a first chamber of fixed volume for receiving sample gas tapped from the pipeline, the sample gas being maintained at substantially the same temperature as the pipeline gas flowing temperature when contained in the first chamber;

a first pressure sensor for measuring the pressure of the sample gas in the first chamber;

a first temperature sensor for measuring the temperature of the sample gas in the first chamber;

a first valve for controlling the flow of sample gas to the first chamber;

a flow restrictor located downstream of the first chamber through which sample gas flowing from the first chamber flows;

a pressure regulator located downstream of the first chamber and upstream of the flow restrictor for reducing the pressure of sample gas flowing from the first chamber before it flows to the flow restrictor so that flow from the first chamber through the flow restrictor is maintained at a substantially constant rate; and a controller for receiving signals from the first pressure sensor and the temperature sensor, for deriving a ratio $$\frac{\rho_f}{\rho_b}$$

of a density $\rho_f$ of the pipeline gas at the flowing temperature and pressure compared to a density $\rho_b$ of the pipeline gas at the base temperature and pressure, and for deriving the base condition volumetric flow rate of the pipeline gas $Q_b$ by multiplying the flowing condition volumetric flow rate of the pipeline gas $Q_f$ by the ratio $$\frac{\rho_f}{\rho_b}.$$

13. A flowmeter as recited in claim 12 wherein the flow restrictor is a sonic nozzle having an inlet and the pressure regulator reduces the pressure of the sample gas flowing from the first chamber to a pressure that is sufficient to maintain critical flow through the sonic nozzle.

14. A flowmeter as recited in claim 13 further comprising:
a second pressure sensor for measuring the pressure of the sample gas at the sonic nozzle inlet; and
wherein the controller further receives a signal from the second pressure sensor.

* * * * *